(12) United States Patent
Ray et al.

(10) Patent No.: US 10,261,006 B2
(45) Date of Patent: Apr. 16, 2019

(54) METHOD OF ESTIMATING CLOUD PARTICLE SIZES USING LIDAR RATIO

(71) Applicant: Rosemount Aerospace Inc., Burnsville, MN (US)

(72) Inventors: Mark Ray, Burnsville, MN (US); Kaare Josef Anderson, Farmington, MN (US)

(73) Assignee: Rosemount Aerospace, Inc., Burnsville, MN (US)

( * ) Notice: Subject to any disclaimer, the term of this patent is extended or adjusted under 35 U.S.C. 154(b) by 5 days.

(21) Appl. No.: 15/216,340

(22) Filed: Jul. 21, 2016

(65) Prior Publication Data
US 2018/0024036 A1 Jan. 25, 2018

(51) Int. Cl.
*G01N 15/02* (2006.01)
*G01W 1/00* (2006.01)
(Continued)

(52) U.S. Cl.
CPC ........ *G01N 15/0211* (2013.01); *G01S 7/4812* (2013.01); *G01S 7/499* (2013.01);
(Continued)

(58) Field of Classification Search
CPC .... G01N 21/49; G01N 21/21; G01N 15/1434; G01N 2201/0697; G01N 2201/06113;
(Continued)

(56) References Cited

U.S. PATENT DOCUMENTS 5,243,185 A * 9/1993 Blackwood .......... G01N 21/211
250/225
5,546,183 A 8/1996 Fegley et al.
(Continued)

FOREIGN PATENT DOCUMENTS

EP 2518529 A2 10/2012
EP 2587278 A1 5/2013

OTHER PUBLICATIONS

Wang, X. "An algorithm to determine cirrus properties from analysis of multiple-scattering influence on lidar signals", Applied Physics B: Laser and Optics, published Feb. 24, 2005, 7 pages.
(Continued)

*Primary Examiner* — Sang H Nguyen
(74) *Attorney, Agent, or Firm* — Kinney & Lange, P.A.

(57) ABSTRACT

Apparatus and associated methods relate to determining sizes of water particles in a cloud atmosphere based on a detected portion of signals generated from a single monochromatic source and backscattered by water particles in a cloud atmosphere. A backscatter coefficient and an optical extinction coefficient are calculated, based on the detected portion of signals generated from the monochromatic source and backscattered by water particles in the cloud atmosphere. A LIDAR ratio—a ratio of the optical extinction coefficient to the backscatter coefficient, is calculated. Sizes of water particles in the cloud atmosphere are estimated based on the LIDAR ratio. An output signal indicative of the estimated sizes of water particles in the cloud atmosphere is generated. Estimating sizes of water particles using signals from a single monochromatic source advantageously can alert a pilot of an aircraft of cloud conditions, without requiring multi-chromatic sources.

17 Claims, 6 Drawing Sheets

(51) Int. Cl.
*G01S 17/95* (2006.01)
*G01S 7/481* (2006.01)
*G01S 7/499* (2006.01)
*G01N 15/00* (2006.01)

(52) U.S. Cl.
CPC ............... *G01S 17/95* (2013.01); *G01W 1/00* (2013.01); *G01N 2015/0046* (2013.01); *Y02A 90/19* (2018.01)

(58) Field of Classification Search
CPC ....... G01N 2201/12; G01N 2201/4972; G01N 15/0211; G01N 2015/0046; B64D 15/20; G01S 17/95; G01S 7/449; G01S 7/4802; G01S 7/4815; G01S 7/4865; Y02A 90/19
See application file for complete search history.

(56) References Cited

U.S. PATENT DOCUMENTS

| | | | |
|---|---|---|---|
| 5,767,519 A * | 6/1998 | Gelbwachs | G01N 21/3504 250/338.5 |
| 5,838,239 A * | 11/1998 | Stern | B64D 15/20 340/583 |
| 6,778,271 B2 | 8/2004 | Watson et al. | |
| 7,986,408 B2 | 7/2011 | Ray et al. | |
| 8,269,950 B2 | 9/2012 | Spinelli et al. | |
| 8,338,785 B2 | 12/2012 | Ray | |
| 8,502,975 B2 | 8/2013 | Roy et al. | |
| 9,116,243 B1 * | 8/2015 | Brown | G01S 17/95 |
| 2010/0026981 A1 * | 2/2010 | Spinelli | G01N 21/538 356/4.01 |
| 2010/0110431 A1 * | 5/2010 | Ray | B64D 15/20 356/342 |
| 2011/0058167 A1 * | 3/2011 | Knox | G01N 15/06 356/338 |
| 2012/0274938 A1 * | 11/2012 | Ray | B64D 15/20 356/342 |
| 2013/0103317 A1 * | 4/2013 | Ray | G01S 17/95 702/3 |
| 2015/0070700 A1 * | 3/2015 | Ray | G01S 17/95 356/342 |

OTHER PUBLICATIONS

Extended European Search Report, for European Patent Application No. 17182590.4, dated Jan. 3, 2018, 9 pages.

* cited by examiner

METHOD OF ESTIMATING CLOUD PARTICLE SIZES USING LIDAR RATIO

BACKGROUND

Various cloud conditions can present risks to aircraft that are traveling through them. If the temperature of a cloud atmosphere is below the freezing point for water, water droplets can become super-cooled liquid droplets. These super-cooled liquid droplets can then undergo a liquid-to-solid phase change upon impact with an aircraft surface. Ice accretes at different surface regions for different sizes of the super-cooled liquid droplets in the cloud atmosphere. Thus, characterizing the sizes of super-cooled water droplets in a cloud atmosphere can facilitate prediction of surface regions where ice will accrete as well as providing alerts of potentially dangerous conditions to a pilot.

Super-cooled small water droplets tend to form ice only on leading edges of an aircraft's exterior surface. Super-cooled Large water Droplets (SLDs), however, can strike the leading edge of a wing and run back past the icing protection systems, or can traverse airflow vectors and strike surfaces aft of these leading edges. Ice that forms on unprotected surface regions can severely alter the aerodynamics of the aircraft. Such ice accretion may cause aircraft stall or result in unpredictable aircraft control variation that might lead to flight issues. When in a cloud, ice can form on control surfaces and/or lift surfaces.

Not every cloud, however, has a significant population of SLDs. Different clouds and different atmospheric conditions may be accompanied by various water droplet size distributions, different ice/liquid ratios, etc., some of which may be entirely safe to an aircraft, while others may not be safe. Such water droplet size distributions and ice/liquid ratios may be measured as cloud metrics using various types of instruments.

Some aircraft are equipped with Light Detection and Ranging (LIDAR) systems to measure these cloud metrics. Such systems may determine sizes of water droplets using two lasers that probe the cloud atmosphere. Each of the two lasers probe the cloud atmosphere using light of different wavelengths. The wavelengths can be selected such that the light absorption within a cloud atmosphere is different for the different wavelengths. Using the differences in the backscatter signal for the different wavelengths, particle sizes can be determined for water droplets and for ice crystals. Such systems are complex, as two lasers are required for droplet size measurement. A simpler system would be beneficial to perform measurement of sizes of super-cooled water droplets in a cloud atmosphere.

SUMMARY

Apparatus and associated devices relate to a system for measuring an effective size of water particles in a cloud atmosphere. The system includes a laser configured to generate a pulse of light of a wavelength and to direct the pulse of light into the cloud atmosphere. The system includes an optical detector configured to detect a portion of the pulse of light backscattered by the water particles in the cloud atmosphere. The system also includes a cloud metric calculator configured to determine, based on the detected portion of the pulse of light backscattered by the water particles in the cloud atmosphere, an optical extinction coefficient and a backscatter coefficient. The cloud metric calculator is further configured to estimate, based on a ratio of the determined optical extinction coefficient to the determined backscatter coefficient, the effective size of the water particles in the cloud atmosphere.

Some embodiments relate a method for measuring an effective size of water particles in a cloud atmosphere. The method includes generating a pulse of light of a wavelength. The method includes directing the generated pulse of light into the cloud atmosphere. The method includes detecting a portion of the pulse of light backscattered by the water particles in the cloud atmosphere. The method includes determining, based on the detected portion of the pulse of light backscattered by the water particles in the cloud atmosphere, an optical extinction coefficient and a backscatter coefficient. The method includes estimating, based on a ratio of the determined optical extinction coefficient to the determined backscatter coefficient, the effective size of the water particles in the cloud atmosphere. The method also includes generating an output signal indicative of the estimated effective size of the water particles in the cloud atmosphere.

Some embodiments relate to a system for measuring an effective size of water particles in a cloud atmosphere. The system includes a laser, a signal detector, one or more processors, and computer-readable memory. The computer-readable memory is encoded with instructions that, when executed by the one or more processors, cause the system to emit a pulse of light from the laser. The computer-readable memory is encoded with instructions that, when executed by the one or more processors, cause the system to receive, from the signal detector, a signal indicative of a detected portion of the emitted pulse of light backscattered by the water particles in the cloud atmosphere. The computer-readable memory is encoded with instructions that, when executed by the one or more processors, cause the system to determine, based on the received signal indicative of the detected portion of the emitted pulse of light backscattered by the water particles in the cloud atmosphere, an optical extinction coefficient and a backscatter coefficient. The computer-readable memory is encoded with instructions that, when executed by the one or more processors, cause the system to estimate, based on a ratio of the determined optical extinction coefficient to the determined backscatter coefficient, the effective size of the water particles in the cloud atmosphere. The computer-readable memory is encoded with instructions that, when executed by the one or more processors, also cause the system to generate an output signal indicative of the estimated effective size of the water particles in the cloud atmosphere.

DETAILED DESCRIPTION

Apparatus and associated methods relate to determining sizes of water particles in a cloud atmosphere based on a detected portion of signals generated from a single monochromatic source and backscattered by water particles in a cloud atmosphere. A backscatter coefficient and an optical extinction coefficient are calculated, based on the detected portion of signals generated from the monochromatic source and backscattered by water particles in the cloud atmosphere. A LIDAR ratio—a ratio of the optical extinction coefficient to the backscatter coefficient, is calculated. Sizes of water particles in the cloud atmosphere are estimated based on the LIDAR ratio. An output signal indicative of the estimated sizes of water particles in the cloud atmosphere is generated. Estimating sizes of water particles using signals from a single monochromatic source advantageously can alert a pilot of an aircraft of cloud conditions, without requiring multi-chromatic sources.

Figure 1:
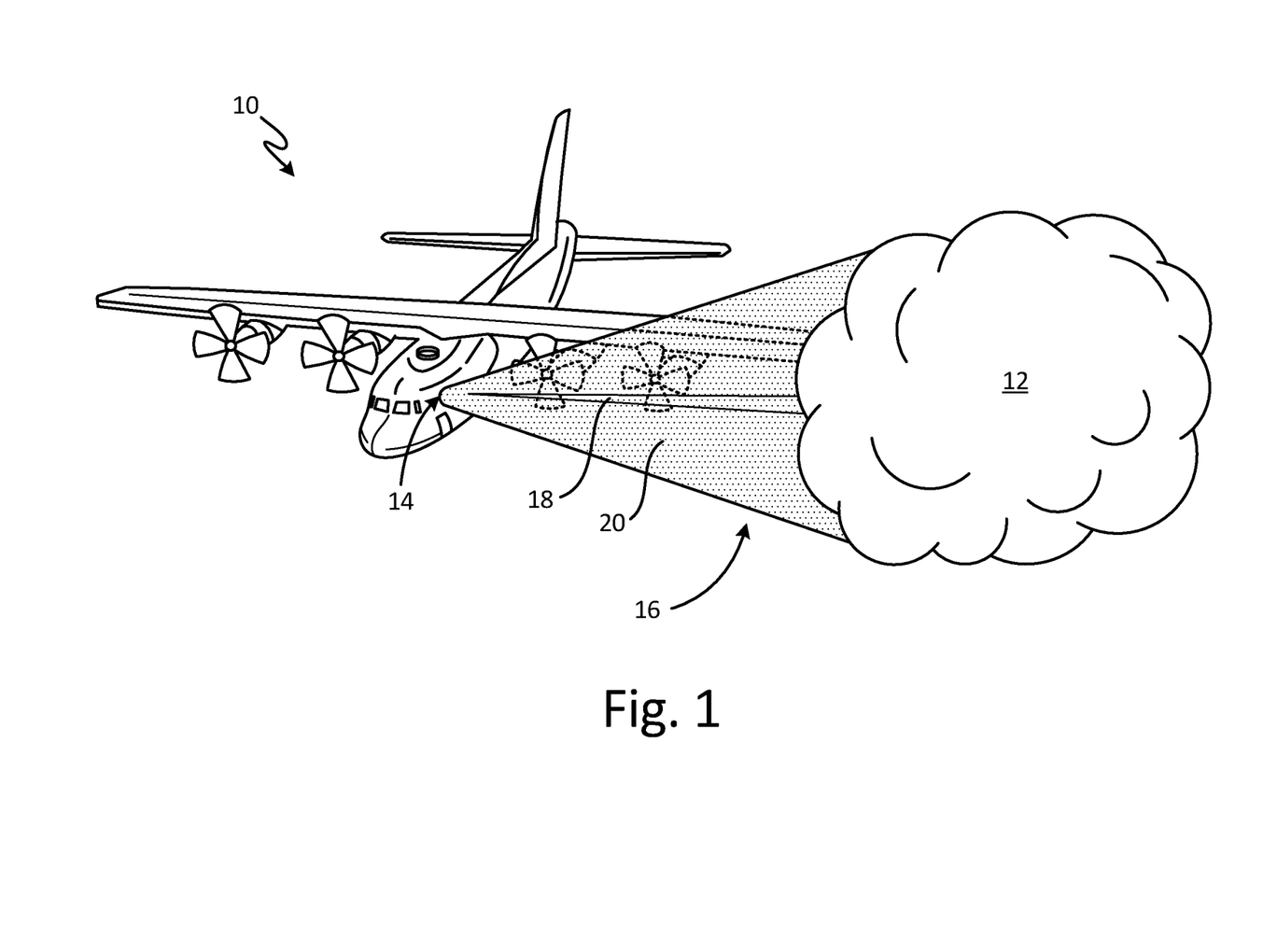
FIG. 1 is a schematic view of an aircraft equipped with an exemplary system for measuring sizes of water particles in a cloud atmosphere.

FIG. 1 is a schematic view of an aircraft equipped with an exemplary system for measuring sizes of water particles in a cloud atmosphere. In FIG. 1, aircraft 10 is traveling through cloud atmosphere 12. Aircraft 10 is equipped with cloud conditions measurement system 14. Cloud conditions measurement system 14 has a single laser that generates a pulse of light for probing cloud atmosphere 12 with optical beam 16. Optical beam 16 can be collimated as indicated in beam pattern 18 or uncollimated as indicated in beam pattern 20. Water particles of cloud atmosphere 12 backscatter a portion of optical beam 16. Cloud conditions measurement system 14 includes an optical detector to detect the portion of optical beam 16 backscattered by the water particles in cloud atmosphere 12. This detected signal can be modeled by the LIDAR signal model. Various model coefficients (or parameters) of the LIDAR signal model can be determined from (or fit to) a signal indicative of the detected portion of optical beam 16 backscattered by the water particles in cloud atmosphere 12. Such model coefficients that can be determined (or fit) include an optical extinction coefficient and a backscatter coefficient. The ratio of the optical extinction coefficient and the backscatter coefficient can be called the LIDAR ratio.

The LIDAR ratio is indicative of an effective size of water particles in a characteristic distribution of sizes of water particles in cloud atmosphere 12. Cloud atmospheres, such as cloud atmosphere 12, can be composed of water droplets having various distributions of water-droplet sizes. The term 'effective size' can refer to a metric characteristic of the distribution of water droplets that compose cloud atmosphere 12. For example effective size can be a mean size, a median size, or a mode of the distribution of water droplets. An effective size can correspond to a size of the water droplets that most reflect a probing signal, for example.

Figure 2:
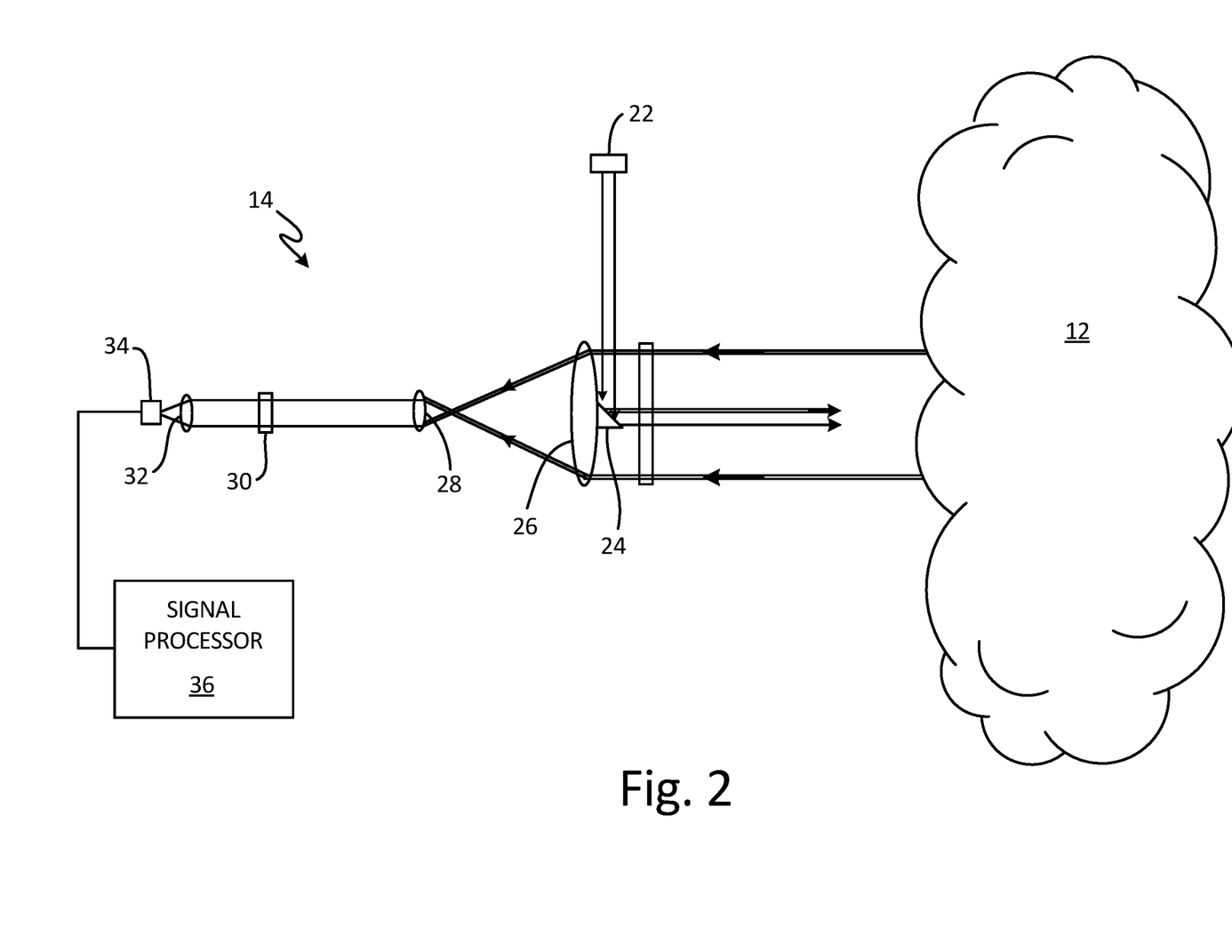
FIG. 2 is a schematic diagram of a monochromatic system for measuring sizes of water particles in a cloud atmosphere.

FIG. 2 is a schematic diagram of a monochromatic system for measuring sizes of water particles in a cloud atmosphere. In FIG. 2, cloud conditions measurement system 14 is depicted probing cloud atmosphere 12. Cloud conditions measurement system 14 shown in FIG. 2 is a collimated embodiment that includes laser diode 22, turning mirror 24, objective lens 26, collimator lens 28, bandpass filter 30, condenser lens 32, optical detector 34, and signal processor 36. Cloud conditions measurement system 14 probes cloud atmosphere 12 using collimated beams of optical energy of a single wavelength having a single initial polarization. In some embodiments, an uncollimated optical system can be used to probe a larger volume of cloud atmosphere 12.

Laser diode 22 generates pulses of optical energy of a specific wavelength or color. The pulses of optical energy generated by laser diode 22 are directed by turning mirror 24 into cloud atmosphere 12. A portion of these pulses of optical energy can be backscattered by water particles of cloud atmosphere 12. The portion of the pulses of optical energy backscattered by water particles of cloud atmosphere 12 are focused and collimated by objective lens 26 and collimator lens 28. The collimated beam passes through bandpass filter 30 and is focused onto optical detector 34 via condenser lens 32.

Optical detector 34 generates a signal (e.g., a backscatter signal) indicative of the portion of the pulses of optical energy backscattered by clout atmosphere 12. The signal generated by optical detector 34 is communicated to signal processor 36. Signal processor 36 is configured to fit a LIDAR signal model to the backscatter signal received from the optical detector. Various coefficients and/or parameters of the LIDAR signal model may be determined by a fit of the LIDAR signal model to the backscatter signal. Coefficients of the LIDAR signal model that can be fit to the backscatter signal include a backscatter coefficient and an optical extinction coefficient.

Signal processor 36 can calculate a LIDAR ratio from the coefficients that are fit to the backscatter signal. A LIDAR ratio can be calculated by taking a ratio of the optical extinction coefficient to the backscatter coefficient. The calculated LIDAR ratio can be indicative of an effective size of water particles that backscattered the optical energy. Signal processor 36 can thus estimate, using the calculated LIDAR ratio, an effective size of water droplets in cloud atmosphere 12.

Figure 3:
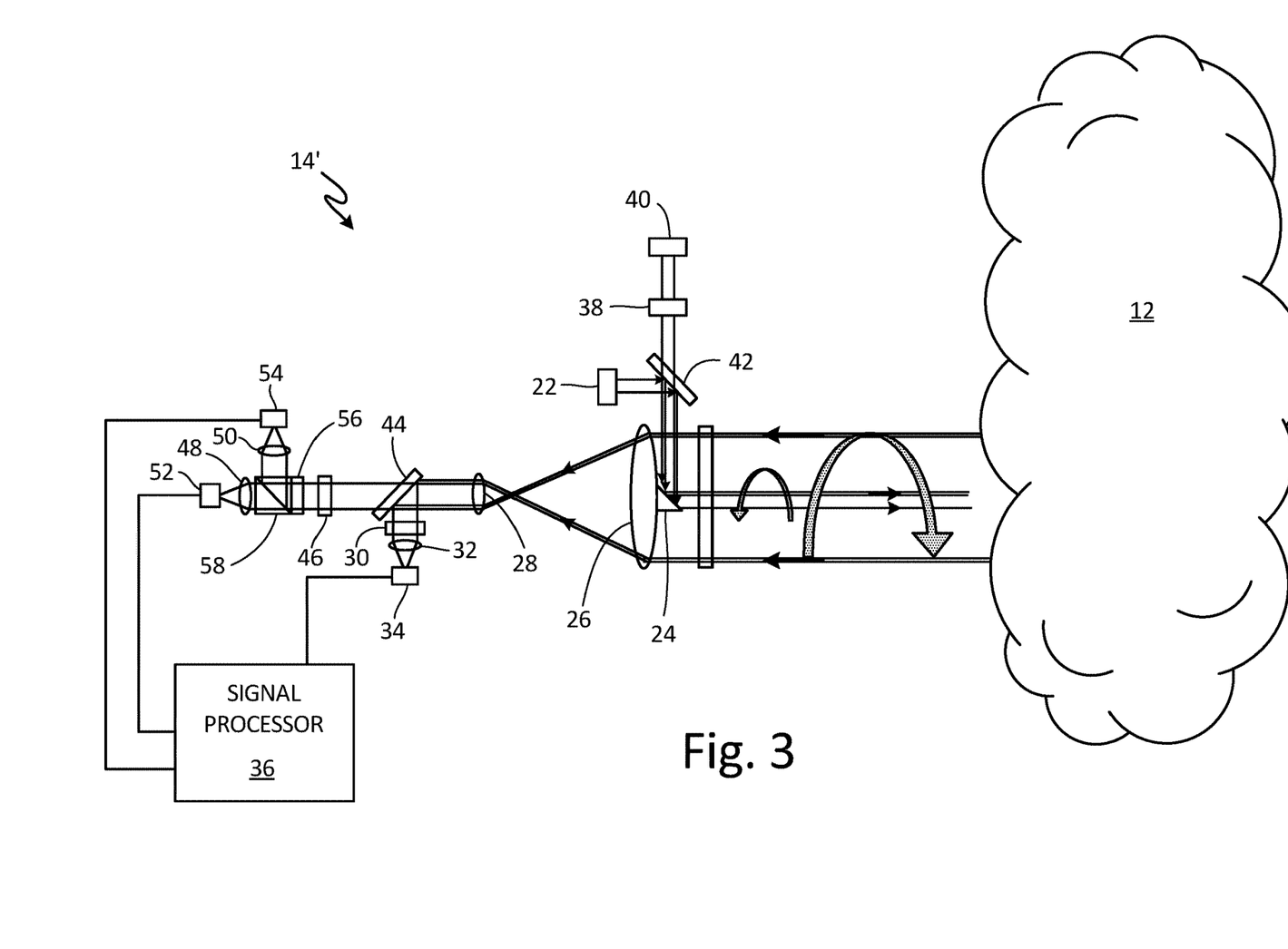
FIG. 3 is a schematic diagram of a multichromatic system for measuring sizes of water particles in a cloud atmosphere.

FIG. 3 is a schematic diagram of a multichromatic system for measuring various cloud metrics. Cloud conditions measurement system 14' depicted in FIG. 3, adds multichromatic and polarizing capabilities to cloud conditions measurement system 14 depicted in FIG. 2. Cloud conditions measurement system 14' includes many of the same elements as cloud conditions measurement system 14 of FIG. 2, including laser diode 22, turning mirror 24, objective lens 26, collimator lens 28, bandpass filter 30, condenser lens 32 and optical detector 34. In addition to these elements, cloud conditions measurement system includes quarter-wave plates 38, 56, laser diode 40 dichroic filter 42, dichroic filter 44, bandpass filter 46, condenser lenses 48, 50, optical detectors 52, 54, and polarizing beam splitter 58.

Cloud conditions measurement system 14' probes cloud atmosphere 12 using collimated beams of optical energy of two dissimilar wavelengths. Using such multichromatic wavelengths of optical energy can provide information used to determine liquid water content of cloud atmosphere 12, such as, for example, a size distribution profile of water particles of the cloud atmosphere.

Laser diode 22 and laser diode 40 generate pulses of optical energy of dissimilar wavelengths in the form of a first collimated beam of a first wavelength. For example, laser diode 22 might generate pulses of optical energy having a first wavelength that corresponds to light having a relatively low water absorption coefficient. In an exemplary embodiment, the first wavelength may be about 905 nm. In such an embodiment, laser diode 40 might be selected so as to generate pulses of optical energy having a second wavelength that corresponds to light having a relatively high water absorption coefficient. For example, various embodiments may have the second wavelength be about 1550 nm.

The pulses of optical energy generated by laser diode 40 are circularly polarized by quarter-wave plate 38. Dichroic filter 42 reflects light having first wavelength, as is generated by laser diode 22, but passes light of second wavelength, as is generated by laser diode 40. Thus, the beam of the first wavelength is reflected by dichroic filter 42 and is then reflected by turning mirror 24. Turning mirror 24 thus directs the collimated beam, which has the first wavelength, into cloud atmosphere 12.

Similar to the operation of cloud conditions measurement system 14 depicted in FIG. 2, a portion of the first optical beam is backscattered by water particles of cloud atmosphere 12. The portion of the pulses of optical energy backscattered by water particles of cloud atmosphere 12 are focused and collimated into a beam by objective lens 26 and collimator lens 28. The collimated beam is reflected by dichroic lens 44, passes through bandpass filter 30, and is focused onto optical detector 34 via condenser lens 32.

Optical detector 34 generates a signal (e.g., a backscatter signal) indicative of the portion of the pulses of optical energy backscattered by clout atmosphere 12. The signal generated by optical detector 34 is communicated to signal processor 36. Signal processor 36 is configured to fit a LIDAR signal model to the backscatter signal received from the optical detector. Various coefficients and/or parameters of the LIDAR signal model may be determined by a fit of the generated signal to the LIDAR signal model. Coefficients of the LIDAR signal model that can be fit to the backscatter signal include a backscatter coefficient and an optical extinction coefficient.

Signal processor 36 can calculate a LIDAR ratio from the coefficients that are fit to the backscatter signal. A LIDAR ratio can be calculated by taking a ratio of the optical extinction coefficient to the backscatter coefficient. Signal processor 36 can then estimate, using the calculated LIDAR ratio, an effective size of water droplets of cloud atmosphere 12.

A second collimated beam having the second wavelength is generated by laser diode 40, is circularly polarized by quarter wave plate 38, passes through dichroic filter 42 and is directed by turning mirror 24 into cloud atmosphere 12. Some of second collimated beam is then backscattered by water particles of cloud atmosphere 12. Backscatter signals corresponding to both first and second collimated beams can be used to determine water droplet sizes and distributions.

The backscattering of the second collimated beam can have two portions each of a different polarization with respect to each other. Different polarizations of the portions of the pulses of optical energy backscattered by water particles of cloud atmosphere may result from the phase of the water particles causing such backscattering (e.g., portions backscattered by ice crystals can have a different polarization than portions backscattered by liquid water droplets). A first portion having a first polarization (e.g., assuming that the second collimated beam is Left-hand Circularly Polarized or LCP, the first backscatter portion will be Right-hand Circularly Polarized or RCP) can result from backscattering of the second collimated beam by liquid water droplets of cloud atmosphere 12. A second portion having a second polarization (e.g., assuming again that the second collimated beam is LCP, the second backscatter portion will also be LCP) can result from backscattering of the second collimated beam by ice particles of cloud atmosphere 12.

This relation between the phase of water particles and backscatter signal polarization is disclosed by Ray et al. in U.S. Pat. No. 7,986,408, filed Nov. 5, 2008, titled "Apparatus and Method for In-Flight Detection of Airborne Water Droplets and Ice Crystals," the entire disclosure (henceforth referred to as "the '408 patent") of which is hereby incorporated by reference. The '408 patent discloses:

> Water droplets ideally act like perfect mirrors and scatter the reflected laser light back on itself without altering the polarization state. If the incident light is horizontally or vertically polarized, the reflected light is likewise horizontally or vertically polarized. Therefore, a backscatter polarization with a relatively low degree of depolarization is indicative of a liquid water cloud. In the case of circular polarization, the direction of the rotating electric field does not change upon reflection, but the change in Poynting vector of the incident wave changes the sense of circular polarization. Hence, an incident beam which is right hand circularly polarized becomes left hand circularly polarized upon reflection, and vice versa.
>
> Ice crystals, on the other hand, tend to alter the polarization state of reflected light, due in part to multiple internal reflections from their facets and in part to the birefringence of ice. Reflected light from airborne ice crystals becomes a mixture of two orthogonal polarization states when the incident light is a pure polarization state. By monitoring both orthogonal polarization states of the backscattered light, it is possible to distinguish water droplets from ice crystals. (Paragraphs [0025, 0026])

Thus, a first portion of the pulses of the second collimated beam backscattered by ice crystals may be left-hand circularly polarized, for example, while a second portion of the pulses of the second collimated beam backscattered by liquid water droplets may be right-hand circularly polarized. Each of these portions of the backscattered second collimated beam is focused by objective lens 26 and collimator lens 28. These focused backscattered optical signal portions then pass through dichroic filter 44. Circularly polarized portions of this backscattered optical signal are then converted to orthogonal planar polarized (e.g., S-polarized and P-polarized) components via quarter-wave plate 56. Polarizing beam splitter 58 directs the planar polarized component corresponding to right-hand circularly polarized light to optical detector 52 via condenser lens 48. Polarizing beam splitter 58 directs the planar component corresponding to left-hand circularly polarized light to optical detector 54 via condenser lens 50.

Output signals indicative of the first and second portions of the backscattered beam are generated by optical detectors 52, 54. These signals can be communicated to signal processor 36. Signal processor 36 can calculate a ratio of the magnitudes of left-hand circularly polarized light and right-hand circularly polarized light based on amplitudes of the detected corresponding planar polarized components. This ratio can be used to calculate an ice/liquid phase ratio of cloud atmosphere 12, for example.

A backscatter coefficient and an optical extinction coefficient can be determined from the first portion of the pulses of optical energy backscattered by ice crystals. A ratio of the optical extinction coefficient to the backscatter coefficient can be used as an indicator of water particle size (e.g., ice crystal size). Similarly, a backscatter coefficient and an optical extinction coefficient can be determined from the second portion of the pulses of optical energy backscattered by liquid water droplets. A ratio of the optical extinction coefficient to the backscatter coefficient can be used as an indicator of water particle size (e.g., liquid water droplet size).

Systems, such as cloud conditions measurement system 14', can use the LIDAR ratio alone and/or in conjunction with other methods of estimating a sizes and distributions of sizes of water droplets in cloud atmosphere 12. For example, water droplet sizes can be estimated using signals from both of the emitted wavelengths.

Figure 4:
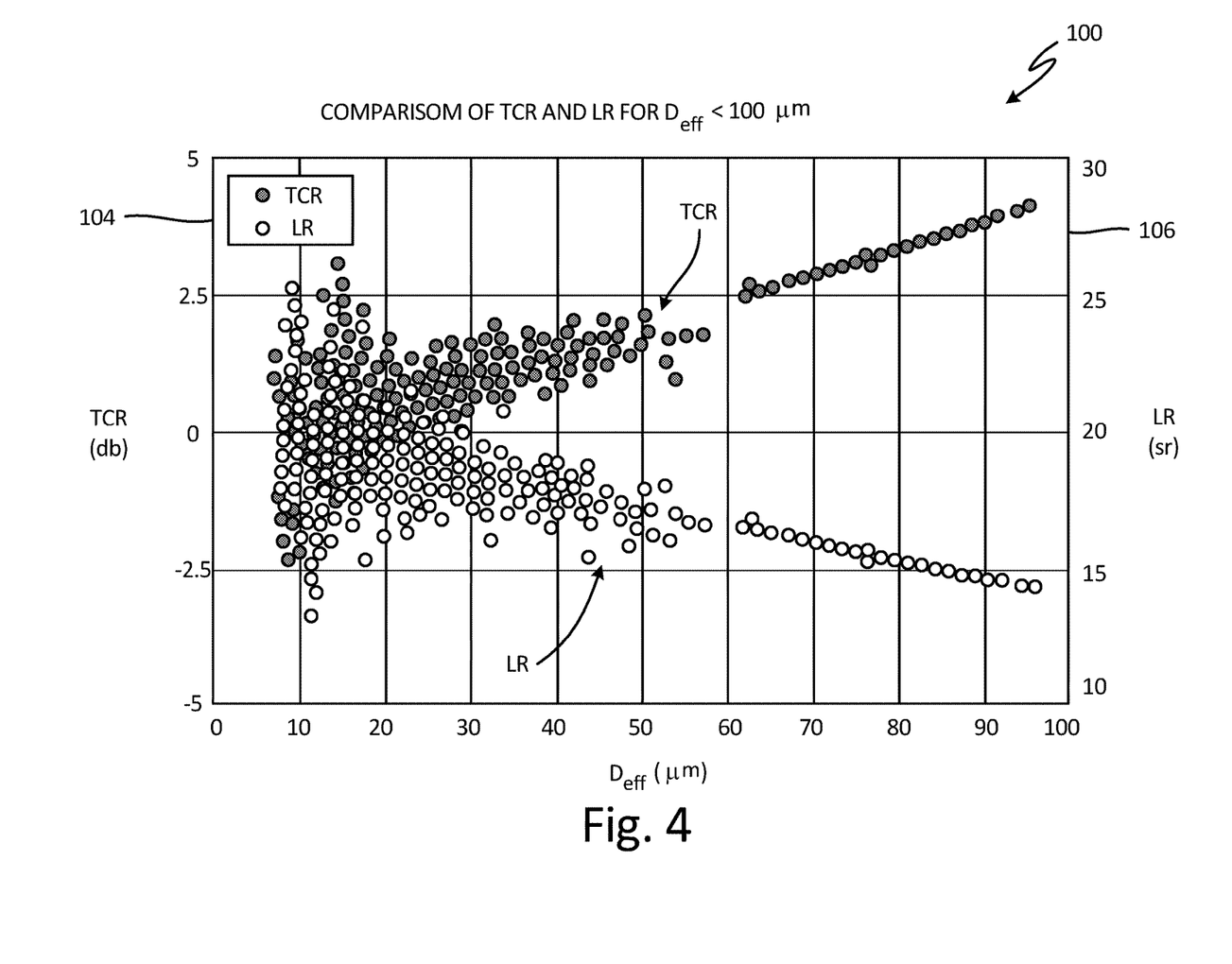
FIG. 4 is a graph of an exemplary relation between LIDAR ratio and size of water particles in a cloud atmosphere.

FIG. 4 is a graph of an exemplary relation between LIDAR ratio and size of water particles in a cloud atmosphere. In FIG. 4, graph 100 includes horizontal axis 102 and two vertical axes 104, 106. Horizontal axis 102 is indicative of an effective particle size ($D_{eff}$). On the left side of graph 100, vertical axis 104 is indicative of a two-color ratio. Such two-color ratios are calculated by taking ratios of coefficients of LIDAR modeled signals from two different backscatter pulses corresponding to light pulses emitted at two different wavelengths or colors. On the right side of graph 100, vertical axis 106 is indicative of a LIDAR ratio of a single backscatter signal (or of an average of a series of monochromatic backscatter signals).

Two relations 108, 110 are depicted in graph 100. $D_{eff}$/TCR relation 108 is the relation between effective particle size $D_{eff}$ and two-color ratio (TCR) of the backscattered signals using LIDAR model coefficients. $D_{eff}$/LR is the relation between effective particle size $D_{eff}$ and LIDAR ratio (LR) (e.g., computed as a ratio of the backscatter coefficient and the optical extinction coefficient). Each of relations $D_{eff}$/TCR and $D_{eff}$/LR demonstrate correlations between $D_{eff}$ and either TCR or LR. The correlation becomes stronger for larger effective particle sizes $D_{eff}$ (e.g., for $D_{eff}$>60 μm).

Figure 5:
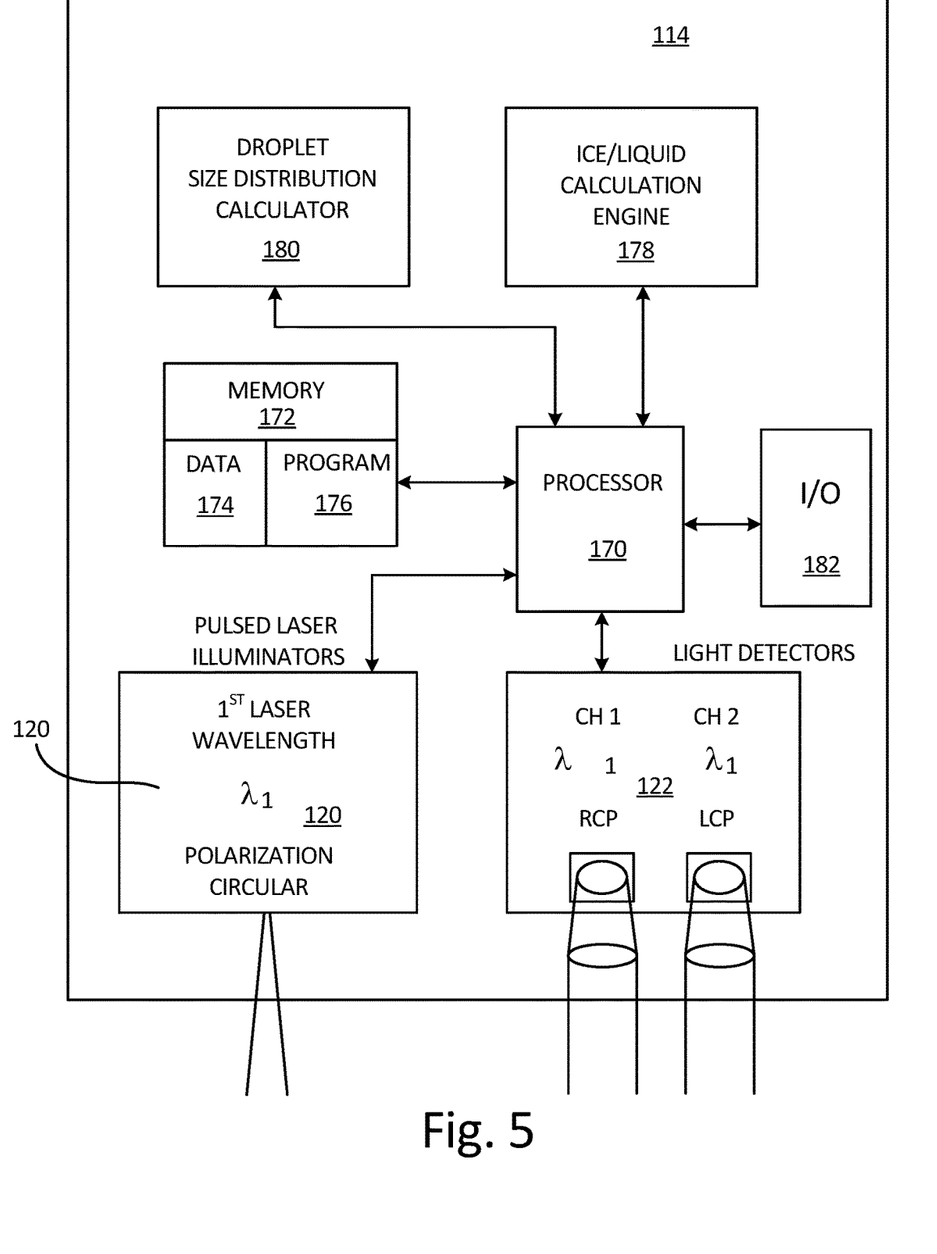
FIG. 5 is a block diagram of an exemplary system for measuring various cloud metrics including measuring sizes of water particles in a cloud atmosphere.

FIG. 5 is a block diagram of an exemplary system for measuring various cloud metrics including measuring sizes of water particles in a cloud atmosphere. In FIG. 5, optical cloud conditions metric calculator 114 includes optical transmitter 120, optical receiver 122, processor 170, memory 172 having data memory locations 174 and program memory locations 176, cloud metrics calculation engine 178, droplet size distribution calculator 180, and input/output interface 182. Optical transmitter 120 generates laser pulses of a specified wavelength and directs the generated pulses to a cloud atmosphere. Optical receiver 122 is then configured to receive light corresponding to one of the generated pulses and backscattered from the cloud atmosphere.

Processor 170 then receives backscattered signals from optical receiver 122. Processor 170 then calculates model parameters based on the received backscattered signals. Processor 170 communicates with data memory locations 174 and program memory locations 176 of memory 172. Processor 170 communicates calculated model parameters to each of droplet size distribution calculator 180 and ice/liquid phase calculation engine 178. Droplet size distribution calculator 180 calculates, based on the calculated model parameters, a size distribution of water particles in the cloud atmosphere. Droplet size distribution calculator 180 then communicates the calculated droplet size distribution to processor 170. In some embodiments, droplet size distribution calculation is performed by processor 170. Droplet size is calculated using a relation between $D_{eff}$ and LIDAR ratio.

Ice/liquid phase calculation engine 178 calculates, based on the calculated model parameters, an ice/liquid ratio of water particles in the cloud formation. Ice/liquid phase calculation engine 178 then communicates the calculated ice/liquid ratio to processor 170. In some embodiments, calculation of an ice/liquid ratio is performed by processor 170. Processor 170 in turn communicates both calculated droplet size distribution and ice/water ratio to a remote system via input/output interface 182. An exemplary remote system can be a cloud parameter indicator located in a cockpit of an aircraft.

Processor 170, in one example, is configured to implement functionality and/or process instructions for execution within cloud conditions metric calculator 114. For instance, processor 170 can be capable of processing instructions stored in program memory locations 176. Examples of processor 170 can include any one or more of a microprocessor, a controller, a digital signal processor (DSP), an application specific integrated circuit (ASIC), a field-programmable gate array (FPGA), or other equivalent discrete or integrated logic circuitry.

Memory 172 can be configured to store information within cloud conditions metric calculator 114 during operation. Memory 172, in some examples, is described as computer-readable storage media. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, memory 172 is a temporary memory, meaning that a primary purpose of memory 172 is not long-term storage. Memory 172, in some examples, is described as volatile memory, meaning that memory 172 do not maintain stored contents when power to cloud conditions metric calculator 114 is turned off. Examples of volatile memories can include random access memories (RAM), dynamic random access memories (DRAM), static random access memories (SRAM), and other forms of volatile memories. In some examples, memory 172 is used to store program instructions for execution by processor 170. Memory 172, in one example, is used by software or applications running on cloud conditions metric calculator 114 (e.g., a software program implementing calculations of cloud conditions metrics) to temporarily store information during program execution.

In some examples, memory 172 can also include one or more computer-readable storage media. Memory 172 can be configured to store larger amounts of information than volatile memory. Memory 172 can further be configured for long-term storage of information. In some examples, memory 172 includes non-volatile storage elements. Examples of such non-volatile storage elements can include magnetic hard discs, optical discs, flash memories, or forms of electrically programmable memories (EPROM) or electrically erasable and programmable (EEPROM) memories.

Input/output interface 182 can be used to communicate information between cloud conditions metric calculator 114 and an aircraft. In some embodiments, such information can include aircraft conditions, flying conditions, and/or atmospheric conditions. In some embodiments, such information can include data processed by cloud conditions metric calculator 114, such as, for example, alert signals. Input/output interface 182 can also include a communications module. Input/output interface 182, in one example, utilizes the communications module to communicate with external devices via one or more networks, such as one or more wireless or wired networks or both. The communications module can be a network interface card, such as an Ethernet card, an optical transceiver, a radio frequency transceiver, or any other type of device that can send and receive information. Other examples of such network interfaces can include Bluetooth, 3G, 4G, and Wi-Fi radio computing devices as well as Universal Serial Bus (USB). In some embodiments, communication with the aircraft can be performed via a communications bus, such as, for example, an Aeronautical Radio, Incorporated (ARINC) standard communications protocol. In an exemplary embodiment, aircraft communication with the aircraft can be performed via a communications bus, such as, for example, a Controller Area Network (CAN) bus.

Figure 6:
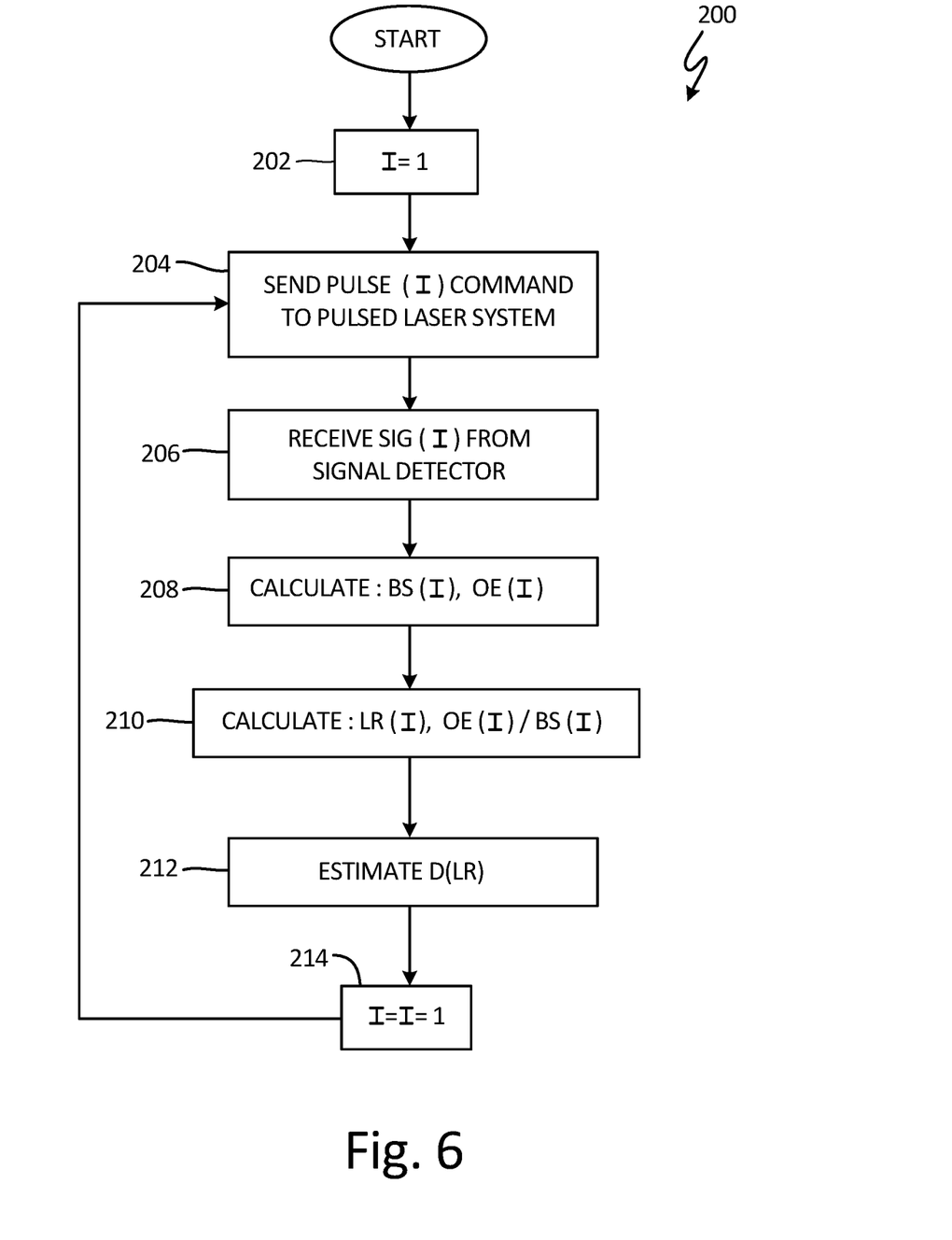
FIG. 6 is a flow chart of an exemplary method for determining sizes of water particles in a cloud atmosphere using LIDAR ratio of a monochromatic backscatter signal.

FIG. 6 is a flow chart of an exemplary method for determining sizes of water particles in a cloud atmosphere using LIDAR ratio of a monochromatic backscatter signal. In FIG. 6, method 200 is depicted from the perspective of processor 170 (shown in FIG. 5). Method 200 begins at step 202 where processor 170 initializes index I. Then, at step 204, processor 170 sends a command signal PULSE(I) to command or initiate optical transmitter 120 to emit a pulse of optical energy. At step 206, microprocessor 170 receives a signal SIG(I) from optical detector 122. Received signal SIG(I) is indicative of a portion of the emitted pulse of optical energy backscattered by water particles in a cloud atmosphere. Then, at step 208, processor 170 calculates backscatter coefficient BS(I) and optical extinction coefficient OE(I). Then, at step 210, calculates a LIDAR ratio LR(I) by taking the ratio of extinction coefficient OE(I) and backscatter coefficient BS(I). Then, at step 212, processor 170 estimates effective particle size D(LR), based on calculated LIDAR ratio LR(I). Then at step 214, processor increments index I and method 200 returns to step 204.

The following are non-exclusive descriptions of possible embodiments of the present invention.

A system for measuring an effective size of water particles in a cloud atmosphere includes a laser configured to generate a pulse of light of a wavelength and to direct the pulse of light into the cloud atmosphere. The system includes an optical detector configured to detect a portion of the pulse of light backscattered by the water particles in the cloud atmosphere. The system also includes a cloud metric calculator configured to determine, based on the detected portion of the pulse of light backscattered by the water particles in the cloud atmosphere, an optical extinction coefficient and a backscatter coefficient. The cloud metric calculator is further configured to estimate, based on a ratio of the determined optical extinction coefficient to the determined backscatter coefficient, the effective size of the water particles in the cloud atmosphere.

The system of the preceding paragraph can optionally include, additionally and/or alternatively a polarizer configured to polarize the pulse of light. Exemplary polarizers can be circular polarizers and/or planar polarizers, for example.

A further embodiment of any of the foregoing systems, wherein the cloud metric calculator can be configured to estimate the effective size of the water particles in the cloud atmosphere using a look-up table. A further embodiment of any of the foregoing systems, wherein the cloud metric calculator can be further configured to calculate, based on the detected portion of the pulse of light backscattered by the water particles in the cloud atmosphere, a concentration of the water particles of the cloud atmosphere. A further embodiment of any of the foregoing systems, wherein the wavelength of the generated pulse of light is between 700 nano-meters and 2.0 micro-meters.

A further embodiment of any of the foregoing systems, wherein the portion of the pulse of light is a first portion of the circularly polarized pulse of light, the first portion having a first polarization. The signal detector can be further configured to detect a second portion of the circularly polarized pulse of light backscattered by the cloud atmosphere, the second portion having a second polarization oppositely oriented to the first polarization. A further embodiment of any of the foregoing systems, wherein the cloud metric calculator can be further configured to calculate, based on the detected first signal and the detected second signal, an ice/liquid phase ratio of the droplets in the cloud atmosphere.

A method for measuring an effective size of water particles in a cloud atmosphere includes generating a pulse of light of a wavelength. The method includes directing the generated pulse of light into the cloud atmosphere. The method includes detecting a portion of the pulse of light backscattered by the water particles in the cloud atmosphere. The method includes determining, based on the detected portion of the pulse of light backscattered by the water particles in the cloud atmosphere, an optical extinction coefficient and a backscatter coefficient. The method includes estimating, based on a ratio of the determined optical extinction coefficient to the determined backscatter coefficient, the effective size of the water particles in the cloud atmosphere. The method also includes generating an output signal indicative of the estimated effective size of the water particles in the cloud atmosphere.

The method of the preceding paragraph can optionally include, additionally and/or alternatively, any one or more of the following features, configurations and/or additional steps:

A further embodiment of the foregoing method can further include the step of calculating, based on the detected portion of the pulse of light backscattered by the water particles in the cloud atmosphere, a concentration of the water particles in the cloud atmosphere. A further embodiment of any of the foregoing methods can further include the step of polarizing the generated pulse of light, such that the pulse of light directed into the cloud atmosphere is polarized.

A further embodiment of any of the foregoing methods, wherein estimating, based on a ratio of the determined optical extinction coefficient to the determined backscatter coefficient, the effective size of the water particles in the cloud atmosphere can include using a look-up table in which the ratio of the determined optical extinction coefficient to the determined backscatter coefficient is correlated to the effective size of water particles in the cloud atmosphere.

A further embodiment of any of the foregoing methods, wherein the wavelength of the generated pulse of light can be between 700 nano-meters and 2.0 micro-meters. In some embodiments, the portion of the pulse of light backscattered by the water particles in the cloud atmosphere is a first portion of the pulse of the circularly polarized light backscattered by the water particles in the cloud atmosphere, the first portion having a first polarization. A further embodiment of any of the foregoing methods can detecting a second portion of the circularly polarized pulse of light backscattered by the water particles in the cloud atmosphere, the second portion having a second polarization oppositely oriented to the first polarization. A further embodiment of any of the foregoing methods can include calculating, based on the detected first portion and the detected second portion, an ice/liquid phase ratio of the droplets in the cloud atmosphere.

A system for measuring an effective size of water particles in a cloud atmosphere includes a laser, a signal detector, one or more processors, and computer-readable memory. The computer-readable memory is encoded with instructions that, when executed by the one or more processors, cause the system to emit a pulse of light from the laser. The computer-readable memory is encoded with instructions that, when executed by the one or more processors, cause the system to receive, from the signal detector, a signal indicative of a detected portion of the emitted pulse of light backscattered by the water particles in the cloud atmosphere. The computer-readable memory is encoded with instructions that, when executed by the one or more processors, cause the system to determine, based on the received signal indicative of the detected portion of the emitted pulse of light backscattered by the water particles in the cloud atmosphere, an optical extinction coefficient and a backscatter coefficient. The computer-readable memory is encoded with instructions that, when executed by the one or more processors, cause the system to estimate, based on a ratio of the determined optical extinction coefficient to the determined backscatter coefficient, the effective size of the water particles in the cloud atmosphere. The computer-readable memory is encoded with instructions that, when executed by the one or more processors, also cause the system to generate an output signal indicative of the estimated effective size of the water particles in the cloud atmosphere.

The system of the preceding paragraph can optionally include, additionally and/or alternatively, any one or more of the following features, configurations and/or additional components:

A further embodiment of the foregoing system can include a polarizer configured to polarize the pulse of light emitted from the laser. Exemplary polarizers can be circular polarizers and/or planar polarizers, for example.

A further embodiment of any of the foregoing systems, wherein estimating, based on a ratio of the determined optical extinction coefficient to the determined backscatter coefficient, sizes of the water particles in the cloud atmosphere can include using a look-up table in which the ratio of the determined optical extinction coefficient to the determined backscatter coefficient is correlated to the effective size of water particles.

A further embodiment of any of the foregoing systems, wherein the computer-readable memory can be further encoded with instructions that, when executed by the one or more processors, can cause the system to calculate, based on the detected portion of the pulse of light backscattered by the water particles in the cloud atmosphere, a concentration of the water particles in the cloud atmosphere. A further embodiment of any of the foregoing systems, wherein the emitted pulse of light can have a wavelength between 700 nano-meters and 2.0 micrometers.

In some embodiments, the portion of the pulse of light backscattered by the water particles in the cloud atmosphere can be a first portion of the polarized pulse of light backscattered by the water particles in the cloud atmosphere. A further embodiment of any of the foregoing systems, wherein the computer-readable memory can be further encoded with instructions that, when executed by the one or more processors, can cause the system to detect a second portion of the circularly polarized pulse of light backscattered by the water particles in the cloud atmosphere, the second portion having a second polarization oppositely oriented to the first polarization. A further embodiment of any of the foregoing systems, wherein the computer-readable memory can be further encoded with instructions that, when executed by the one or more processors, can cause the system to calculate, based on the detected first portion and the detected second portion, an ice/liquid phase ratio of the droplets in the cloud atmosphere.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A system for measuring an effective size of water particles in a cloud atmosphere, the system comprising:
   a laser configured to generate a pulse of light of a wavelength and to direct the pulse of light into the cloud atmosphere;
   an optical detector configured to detect a portion of the pulse of light backscattered by the water particles in the cloud atmosphere; and
   a cloud metric calculator configured to determine, based on the detected portion of the pulse of light backscattered by the water particles in the cloud atmosphere, an optical extinction coefficient and a backscatter coefficient,
   wherein the cloud metric calculator is further configured to estimate, based on a look-up table and a ratio of the determined optical extinction coefficient to the determined backscatter coefficient, the effective size of the water particles in the cloud atmosphere.

2. The system of claim 1, wherein the cloud metric calculator is further configured to calculate, based on the detected portion of the pulse of light backscattered by the water particles in the cloud atmosphere, a concentration of the water particles of the cloud atmosphere.

3. The system of claim 1, wherein the wavelength of the generate pulse of light is between 700 nano-meters and 2.0 micro-meters.

4. The system of claim 1, further comprising a polarizer configured to circularly polarize the pulse of light.

5. The system of claim 4, wherein the portion of the pulse of light is a first portion of the circularly polarized pulse of light, the first portion having a first polarization, wherein the signal detector is further configured to detect a second portion of the circularly polarized pulse of light backscattered by the cloud atmosphere, the second portion having a second polarization oppositely oriented to the first polarization.

6. The system of claim 5, wherein the cloud metric calculator is further configured to calculate, based on the detected first signal and the detected second signal, an ice/liquid phase ratio of the droplets in the cloud atmosphere.

7. A method for measuring an effective size of water particles in a cloud atmosphere, the method comprising:
   generating a pulse of light of a wavelength;
   directing the generated pulse of light into the cloud atmosphere;
   detecting a portion of the pulse of light backscattered by the water particles in the cloud atmosphere;
   determining, based on the detected portion of the pulse of light backscattered by the water particles in the cloud atmosphere, an optical extinction coefficient and a backscatter coefficient;
   estimating, based on a look-up table and a ratio of the determined optical extinction coefficient to the determined backscatter coefficient, the effective size of the water particles in the cloud atmosphere; and
   generating an output signal indicative of the estimated effective size of the water particles in the cloud atmosphere.

8. The method of claim 7, further comprising:
calculating, based on the detected portion of the pulse of light backscattered by the water particles in the cloud atmosphere, a concentration of the water particles in the cloud atmosphere.

9. The method of claim 7, wherein the wavelength of the generated pulse of light is between 700 nano-meters and 2.0 micro-meters.

10. The method of claim 7, further comprising:
polarizing the generated pulse of light, such that the pulse of light directed into the cloud atmosphere is polarized.

11. The method of claim 10, wherein the portion of the pulse of light backscattered by the water particles in the cloud atmosphere is a first portion of the pulse of the circularly polarized light backscattered by the water particles in the cloud atmosphere, the first portion having a first polarization, the method further comprising:
detecting a second portion of the circularly polarized pulse of light backscattered by the water particles in the cloud atmosphere, the second portion having a second polarization oppositely oriented to the first polarization.

12. The method of claim 11, further comprising:
calculating, based on the detected first portion and the detected second portion, an ice/liquid phase ratio of the droplets in the cloud atmosphere.

13. A system for measuring an effective size of water particles in a cloud atmosphere, the system comprising:
a laser;
a signal detector;
one or more processors; and
computer-readable memory encoded with instructions that, when executed by the one or more processors, cause the system to:
emit a pulse of light from the laser;
receive, from the signal detector, a signal indicative of a detected portion of the emitted pulse of light backscattered by the water particles in the cloud atmosphere;
determine, based on the received signal indicative of the detected portion of the emitted pulse of light backscattered by the water particles in the cloud atmosphere, an optical extinction coefficient and a backscatter coefficient;
estimate, based on a ratio of the determined optical extinction coefficient to the determined backscatter coefficient, the effective size of the water particles in the cloud atmosphere by using a look-up table in which the ratio of the determined optical extinction coefficient to the determined backscatter coefficient is correlated to the effective size of water particles; and
generate an output signal indicative of the estimated effective size of the water particles in the cloud atmosphere.

14. The system of claim 13, wherein the computer-readable memory further encoded with instructions that, when executed by the one or more processors, cause the system to:
calculate, based on the detected portion of the pulse of light backscattered by the water particles in the cloud atmosphere, a concentration of the water particles in the cloud atmosphere.

15. The system of claim 13, wherein the emitted pulse of light has a wavelength between 700 nano-meters and 2.0 micrometers.

16. The system of claim 13, further comprising a polarized configured to circularly polarize the pulse of light emitted from the laser.

17. The system of claim 16, wherein the portion of the pulse of light backscattered by the water particles in the cloud atmosphere is a first portion of the circularly polarized pulse of light backscattered by the water particles in the cloud atmosphere, the computer-readable memory is further encoded with instructions that, when executed by the one or more processors, cause the system to:
detect a second portion of the circularly polarized pulse of light backscattered by the water particles in the cloud atmosphere, the second portion having a second polarization oppositely oriented to the first polarization; and
calculate, based on the detected first portion and the detected second portion, an ice/liquid phase ratio of the droplets in the cloud atmosphere.

\* \* \* \* \*